(12) United States Patent
Kitt et al.

(10) Patent No.: US 8,324,269 B2
(45) Date of Patent: Dec. 4, 2012

(54) STABLE COMPOSITIONS OF DEHYDROASCORBIC ACID

(75) Inventors: Douglas Q. Kitt, Salt Lake City, UT (US); Jay P. Kitt, Salt Lake City, UT (US)

(73) Assignee: ReCverin LLC, Salt Lake City, UT (US)

( * ) Notice: Subject to any disclaimer, the term of this patent is extended or adjusted under 35 U.S.C. 154(b) by 275 days.

(21) Appl. No.: 12/787,331

(22) Filed: May 25, 2010

(65) Prior Publication Data

US 2011/0046216 A1 Feb. 24, 2011

(51) Int. Cl.
*A01N 43/08* (2006.01)
*A61K 31/34* (2006.01)

(52) U.S. Cl. ...................................... 514/474

(58) Field of Classification Search .................. 514/474
See application file for complete search history.

(56) References Cited

U.S. PATENT DOCUMENTS

2002/0034548 A1\* 3/2002 Parr et al. ...................... 424/489
2007/0190209 A1\* 8/2007 Sinnott ............................ 426/72

\* cited by examiner

*Primary Examiner* — Jeffrey S. Lundgren
*Assistant Examiner* — Michael Schmitt (57) ABSTRACT

The invention relates to stable liquid compositions containing the oxidized form of vitamin C known as dehydroascorbic acid (DHAA). The compositions comprise DHAA and a pharmacologically acceptable liquid organic polyol solvent. The polyol solvent comprises about 50% or greater of the total weight of the composition. The compositions are useful as dietary supplements, skin-enhancers, concentrates, or research solutions.

18 Claims, 8 Drawing Sheets

STABLE COMPOSITIONS OF DEHYDROASCORBIC ACID

BACKGROUND

1. Field of Invention

This invention relates to compositions of matter used as sources of vitamin C in dietary supplementation, skin care products, therapy, research, and manufacturing. More specifically, the invention relates to stable liquid compositions containing the oxidized form of vitamin C known as dehydroascorbic acid.

2. Prior Art

Ever since the elucidation of the chemical structure of vitamin C in the mid-1930's it has been known that vitamin C occurs naturally as two different compounds, namely, ascorbic acid (AA) and an oxidized form of AA called dehydroascorbic acid (DHAA). It also is known that AA and DHAA are unstable compounds. In aqueous solutions, some factors which affect the rate of their destruction include the pH of the solution, and exposure to various metal ions, heat, light and air. It also is known that DHAA is considerably less stable than AA when subjected to comparable conditions. 'Deutsch J C. Dehydroascorbic acid. Review Journal of Chromatography A, 881 (2000) 299-307 ' (Deutsch), incorporated here by reference, states en-equivocally "DHA is more reactive and unstable in solution than AA." Therefore, as a supplement to the diet, or as an ingredient of a topically applied product such as a skin lotion, AA has been the preferred chemical form of vitamin C because of its greater stability. In fact, we do not know of any commercially available dietary or topically applied product wherein DHAA specifically has been utilized as a substantial source of vitamin C.

Also known is that solid AA is far more easily dissolved in water than is solid DHAA, as noted in 'Pecherer B J. The Preparation of Dehydro-L-ascorbic Acid and its Methanol Complex. Am Chem Soc 73 (1951) 3827-3830' (Pecherer) and 'Koliou E K and Ioannou P V. Preparation of dehydro-L-ascorbic acid dimer by air oxidation of L-ascorbic acid in the presence of catalytic amounts of copper(II) acetate and pyridine. Carbohydrate Research 340 (2005) 315-318 ' (Koliou) which are incorporated here by reference. To prepare aqueous solutions of DHAA from the solid form requires prolonged mixing at temperatures well above 37 degrees centigrade. Thus solutions of DHAA are much more difficult to manufacture than solutions of AA. Also, since the conditions to solubilize it efficiently do not exist in the gut of human or other animals, substantial doubt exists about whether the dry, solid form of DHAA can be absorbed when ingested. These are also reasons why DHAA has not been utilized as the source of vitamin C for dietary supplements or topical products.

Around the same time as the chemical structures of AA and DHAA were elucidated in the mid-1930's, the antiscorbutic properties (ability to prevent the disease called scurvy) of both compounds were recognized and generally accepted as being equal or nearly so. The oxidation of AA to DHAA was shown to be reversible both in vitro and in biological systems, so the equivalence of the two compounds could easily be attributed to simple interconversion within an organism. Although a few early investigators did note some peculiar differences in the biological utilization of these two compounds, at least as essential dietary ingredients for humans and certain other species, AA and DHAA were generally considered bioequivalent. The dietary supplement and skin care product industries developed their products using AA (and various more stable derivatives of AA) because of the stability and solubility issues with DHAA, and DHAA has essentially been ignored and forgotten in these industries.

Since the mid-1930's, the volume of research in vitamin C has been enormous, and it is possible that no single subject in the field of biology has been the focus of more research and more scientific journal articles than vitamin C. And since about the mid-1990's, many new discoveries about DHAA have been made. Among these discoveries, those of particular pertinence to the present invention include those which demonstrate that, although the two compounds are equivalent in their antiscorbutic properties, AA and DHAA are not "bioequivalent" in any broad definition of the word. Specifically it is known today that AA and DHAA are absorbed by different mechanisms in the gut; that they accumulate differently in the various tissues of an animal when ingested; that they are absorbed into living cells by completely different mechanisms utilizing different receptors on the cell surface; that the cells of certain important tissues of the human body (e.g., brain) have a very high concentration of vitamin C but completely lack cell surface receptors for AA; that DHAA is absorbed into cells by the same receptors as glucose, which are present on every cell in the human body; that in human skin cells, DHAA is absorbed up to 5 times faster and to levels 2 times higher than is AA; that DHAA is almost instantly converted into AA once it has been absorbed into a cell; that both AA and DHAA have antiviral effects in vitro against viruses that cause disease in humans such as HSV-1 (herpes simplex virus type 1 that causes oral herpes and can cause genital herpes), influenza virus, and poliovirus; and that DHAA has much stronger antiviral effects than does AA. Literature that supports these statements, and is incorporated here by reference, includes 'Savini et al. Dehydroascorbic acid uptake in a human keratinocyte cell line (HaCaT) is glutathione-independent. Biochem J 345 (2000) 665-672 ' (Savini) and 'Furuya et al. Antiviral effects of ascorbic and dehydroascorbic acids in vitro. Int J Mol Med 22 (2008) 541-545' (Furuya).

Thus it can be seen that a solution of DHAA for oral ingestion or topical application, while being a source of vitamin C much like numerous other available products that contain AA, also can provide specific benefits and uses unavailable in any other product on the market today. What is needed is a stable liquid solution of DHAA in an orally and topically acceptable medium.

U.S. Pat. No. 5,140,043 (Dan) discloses topical compositions of ascorbic acid (or a reducing analog of ascorbic acid) in a water-(glycol or polyol) carrier, wherein the ratio of water to glycol/polyol carrier is high (e.g., at least 1:1). These solutions of Darr do not contain DHAA, and Darr is silent as to the stability of the non-reducing compound DHAA in this carrier. We have found that DHAA is not stable in polyol solutions containing such high concentrations of water, which points out that no assumptions about the chemical and physical behavior of DHAA in polyol solutions should be drawn from the behavior of AA in those solutions. While AA and DHAA share certain biological functions, they are two different molecules in regard to their physical and chemical behavior, including stability.

U.S. Pat. No. 6,197,813 (Hegenauer) discloses stable vitamin C compositions of mineral ascorbates in liquid organic polyol solvents having pH values of about 5 to 7, but is silent as to the stability of the non-mineral DHAA in those solvents. These compositions of Hegenaur do not contain DHAA. In fact, these compositions do not even contain a naturally-occurring form of vitamin C, and therefore if these compositions were applied to the skin, vitamin C would not be expected to be absorbed by either the ascorbic acid receptors or the glucose receptors of skin cells.

US Patent Application 2009/0016974 A1 (Pruche et al) discloses DHAA-containing compositions formed "in situ" from ascorbic acid via chemical oxidation and/or via enzymatic oxidation, and a two-component agent thereof. These compositions attempt to overcome the instability of DHAA by preparing it fresh as needed, but they require handling and mixing steps of the two-component agent. The two components must be stored separately. Chemical oxidizers are harsh and can be dangerous, and enzymes are unstable, thus these compositions are problematic in regard to safety and reliability. Since the two components are intended to be combined by the end user, the temperature of the reaction and other conditions necessary for reliable oxidation processes are beyond the control of the manufacturer. Without some separate indicator, the final consumer cannot be assured that the solution prepared by the two-component system actually contains DHAA, because the oxidation of AA to DHAA is not visually or otherwise simply detected. These compositions do not contain DHAA pre-prepared in a stable solution, and Pruche et al is silent as to the stability of DHAA in the disclosed compositions.

OBJECTS AND ADVANTAGES

Several objects and advantages of the present invention are:
a. To provide compositions containing DHAA in a stable form.
b. To provide stable DHAA-containing compositions for topical application to the skin of a human or animal as a source of highly absorbable vitamin C.
c. To provide compositions for topical application that are pharmacologically acceptable and pleasant to use.
d. To provide compositions for topical application that can be applied alone, or mixed with water to provide greater humidifying effect, or mixed with another skin care product to enhance the vitamin C content of that product.
e. To provide compositions containing DHAA for topical application that can also solubilize other skin-enhancing substances that are insoluble in water, such as vitamin E.
f. To provide stable DHAA-containing compositions for dietary supplementation of a human or animal as a source of highly absorbable vitamin C.
g. To provide compositions for dietary supplementation that are pharmacologically acceptable and pleasant to use.
h. To provide compositions for dietary supplementation that can be taken orally alone, or mixed with water or some other liquid, or applied to solid food.
i. To provide stable DHAA-containing concentrates for manufacturing of other products.
j. To provide stable DHAA-containing compositions that can be conveniently used in research, for example in chemical studies, or in microbial culture or tissue culture.
k. To provide stable DHAA-containing compositions that do not require the addition of chemical stabilizers or preservatives.

DESCRIPTION

We have discovered that DHAA is stable in solutions of pure polyol solvents and in solutions wherein the polyol content is greater than about 50 percent. By "stable" is meant that DHAA in these solutions deteriorates very slowly over a sufficient period of time that it can be stored and sold as a dietary supplement or as a skin care product, or as a concentrate for preparing or manufacturing them, with a reasonable shelf life. The solutions are made by oxidizing ascorbic acid that is first dissolved in a pure polyol solvent, or in water, or in some mixture of these liquids. The polyol concentration may be adjusted to about 50% or greater prior to oxidizing the AA or afterwards.

The solutions can also be made by oxidizing AA that is dissolved in an alcohol (e.g., ethanol), and then combining the DHAA-containing alcohol with a polyol solvent. If it is desired that the final solution does not contain alcohol, the alcohol can be removed by evaporating the alcohol from the polyol solvent solution using heat or vacuum, or both.

The solutions can also be made by dissolving solid DHAA in a pure polyol solvent, or in water, or in some mixture of these liquids. The polyol concentration may be adjusted to about 50% or greater prior to dissolving the DHAA or afterwards.

The organic polyol solvents are chosen for pharmaceutical and dietary acceptability, their ability to solubilize the AA and DHAA component, water content, and effect on the stability of the DHAA component. At present we prefer to employ commercially available glycerol which generally contains 5% or less water. In general, we prefer to minimize the water content of the solvent(s), consistent with economic and functional considerations. Other polyols which can be employed include propylene glycol, hexylene glycol, butylene glycol and the almost infinite molecular weight range of polyethylene glycols, as well as so-called sugar alcohols, e.g., sorbitol and xylitol, and mixtures thereof with other polyols.

These solutions can be prepared entirely with one polyol solvent, e.g., glycerol, or mixtures of polyol solvents. The final choice of solvent will depend on economics and other relevant factors.

Methods we have successfully applied for oxidizing the ascorbic acid include the use of halogen or ozone or oxygen/activated charcoal or Fenton's Reagent or ascorbic acid oxidase enzyme. All of these methods are known in the art, as are other methods; the previously cited references Pecherer and Koliou show typical applications of various methods for example. The method by which the oxidation is accomplished is not the determinant factor of the long term stability of the DHAA in the solution, and other methods of oxidation are within the scope of the invention.

AA concentration in solution is commonly measured as the reducing activity of the solution using starch-iodine titration methods that are well-known in the art. AA is also measured by ultra-violet spectrophotometry using a wavelength at which AA absorbs strongly and DHAA does not, typically about 265 nm. This method is also well known in the art. DHAA in solution can be converted into AA by reducing agents such as dithiothreitol (DTT) or tris(2-carboxyethyl)phosphine (TCEP), and its concentration is commonly measured spectrophotometrically as the difference in absorbance of a solution subjected to reduction by DTT or TCEP versus a similar solution that is not subjected to a reducing agent. These methods are also well-known in the art, but see Deutsch for examples. In the description, claims, and the following examples, DHAA in the compositions of the invention is the vitamin C that can be measured by the difference in absorbance at 262 nm using TCEP reducing agent.

The following embodiments are exemplary of the invention:

EXAMPLE 1

In a preferred embodiment of the invention, AA dissolved in glycerol and/or water is oxidized using ozone to produce DHAA solutions. Water-based solutions and glycerol-based solutions may be combined to yield stable DHAA compositions having the desired polyol concentration.

A 15% AA solution in water was prepared by adding 15 grams AA per 100 mL purified water with stirring. A 15% solution of AA in glycerol was prepared by adding 15 grams AA per 100 mL pure USP glycerol and stirring with heat. A corona-discharge type ozone generator with feed-gas of pure oxygen was used to supply an oxidizing gas containing about 5% ozone, and each of the 15% AA solutions was subjected to oxidizing conditions by bubbling the oxidizing gas through the solution using a glass diffuser. The progress of AA oxidation in each solution was monitored by the disappearance of reducing activity as measured by starch-iodine titration. Each solution was subjected to the oxidizing conditions until all (>99%) of the original reducing activity had disappeared. The solution made with pure glycerol was labeled "100% Glycerol," and the solution made with purified water was labeled "100% Water." Portions of these two solutions were combined to produce solutions of various glycerol concentrations by weight, specifically "99% Glycerol," "98% Glycerol," "97% Glycerol," "96% Glycerol," "95% Glycerol", "90% Glycerol," and "50% Glycerol." For example, 99 parts by weight of "100% Glycerol" was combined with 1 part by weight "100% Water" to produce the "99% Glycerol" solution.

Aliquots of each of the solutions prepared above were placed in translucent, screw-capped polyethylene vials and were stored at room temperature. No attempt was made to further protect the vials from ambient indoor light, and each vial contained a headspace of normal air. Each vial was periodically opened to remove a sample for stability testing over the next 229 days. The concentration of DHAA in each sample was measured by spectrometry on each testing day. The initial DHAA concentration of each solution on Day 1 was recorded and assigned a value of 100%, and the concentration on each subsequent stability test day was calculated as the percent remaining of the initial concentration.

FIGS. 1 through 8 show the results of stability testing of the various glycerol-containing solutions; each graph also shows the result of the "100% Water" solution for comparison. It can be seen that DHAA decomposes rapidly in water. By the time the water solution was tested at 20 days, less than 10 percent of the initial amount of DHAA remained. By contrast, DHAA is preserved very well in solutions containing high concentrations of glycerol. In pure glycerol for example, greater than 80% of the initial DHAA concentration remains even after approximately 8 months of storage at room temperature. As the glycerol concentration is reduced, stability is reduced, until only minor improvement is gained at 50% glycerol concentration.

EXAMPLE 2

In another embodiment, a stable DHAA composition is produced by oxidation of AA dissolved in glycerol using exposure to activated charcoal and oxygen as the oxidation method.

A solution of AA in pure USP glycerol was subjected to oxidizing conditions by suspending activated charcoal in the solution and then bubbling pure oxygen through the solution. Oxidation of AA during this process was monitored by starch-iodine titration. After the desired amount of AA had been oxidized, the activated charcoal was removed from the solution by centrifugation and filtration. This solution was labeled "100% Glycerol." A portion of the solution was then placed in a translucent, screw-capped polyethylene vial and was stored at room temperature. No attempt was made to further protect the vial from ambient indoor light, and the vial contained a headspace of normal air. The vial was periodically opened to remove a sample for stability testing over the next 191 days. The concentration of DHAA in the sample was measured by spectrometry on each testing day. The initial DHAA concentration of the solution on Day 1 was recorded and assigned a value of 100%, and the concentration on each subsequent stability test day was calculated as the percent remaining of the initial concentration.

Figure 1:
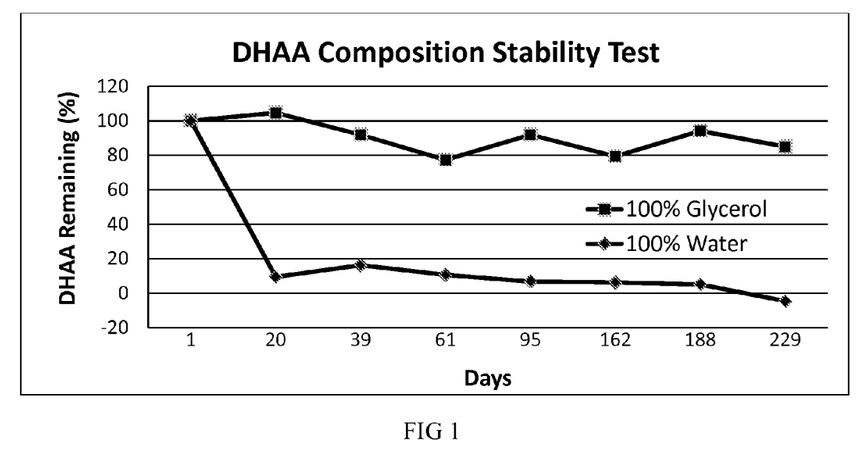
FIGS. 1 to 8 show the DHAA stability of the various compositions described in Example 1 as compared with DHAA prepared similarly in water.
Figure 2:
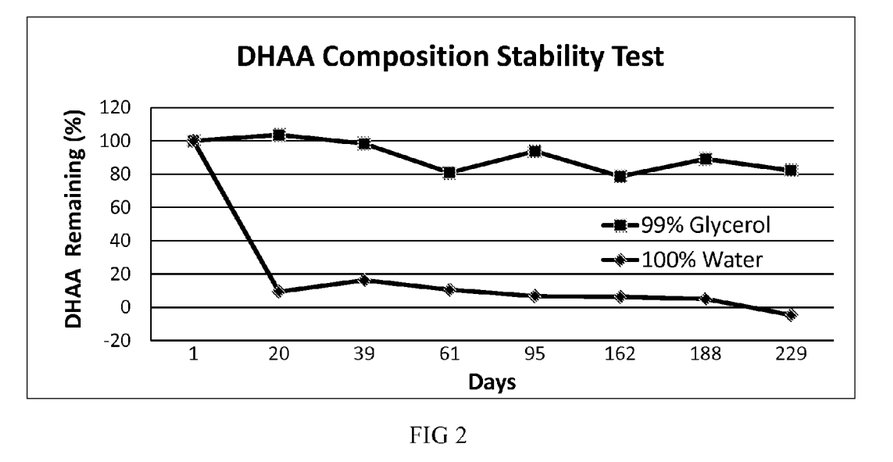
Figure 3:
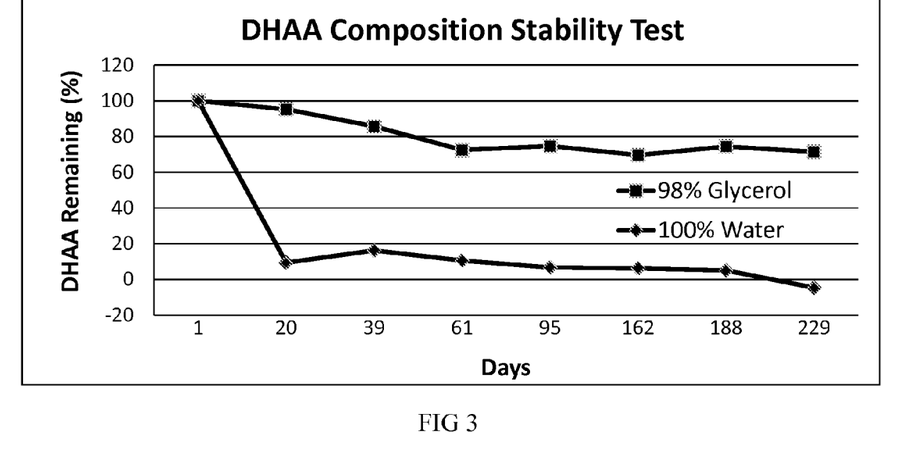
Figure 4:
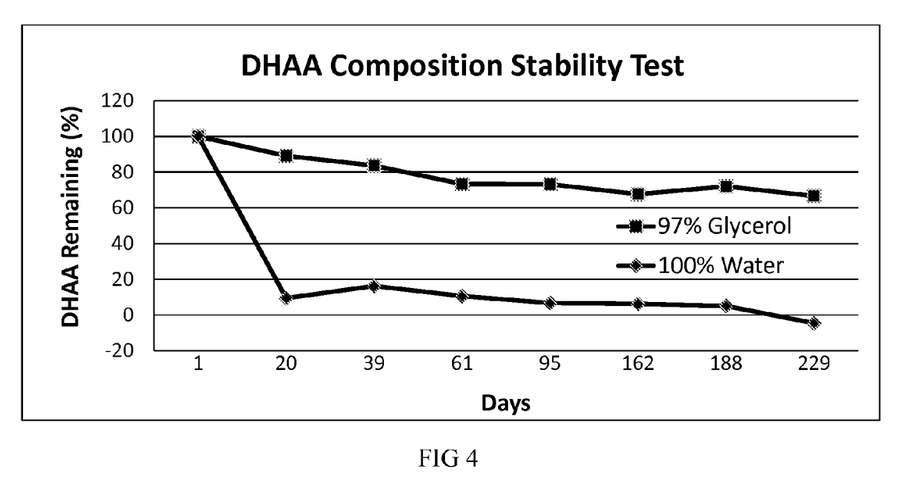
Figure 5:
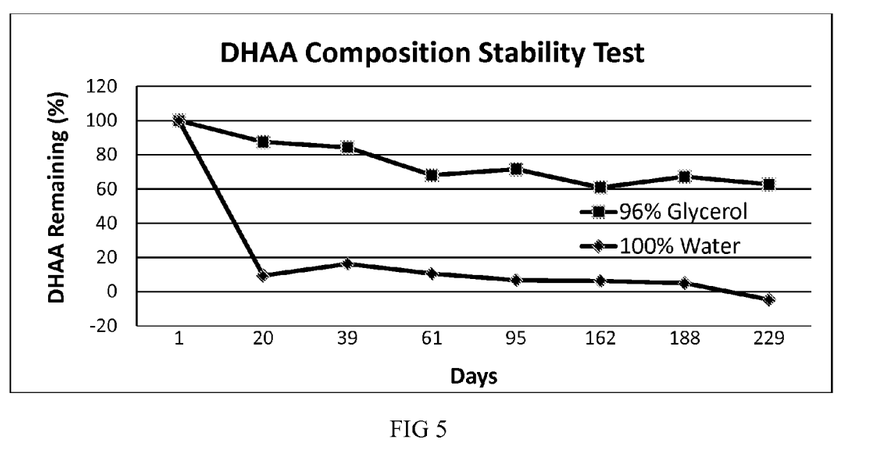
Figure 6:
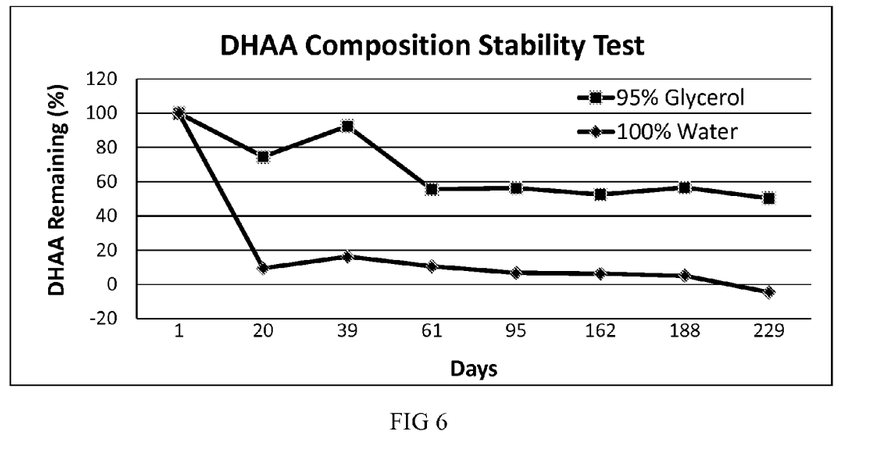
Figure 7:
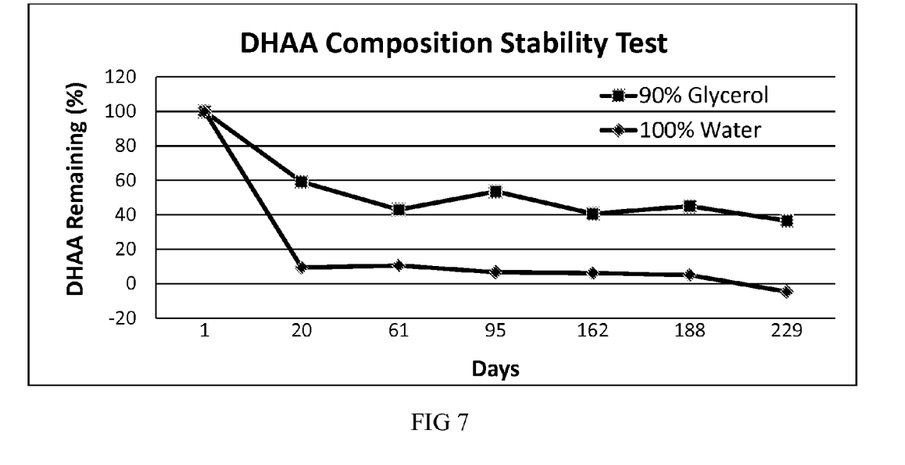
Figure 8:
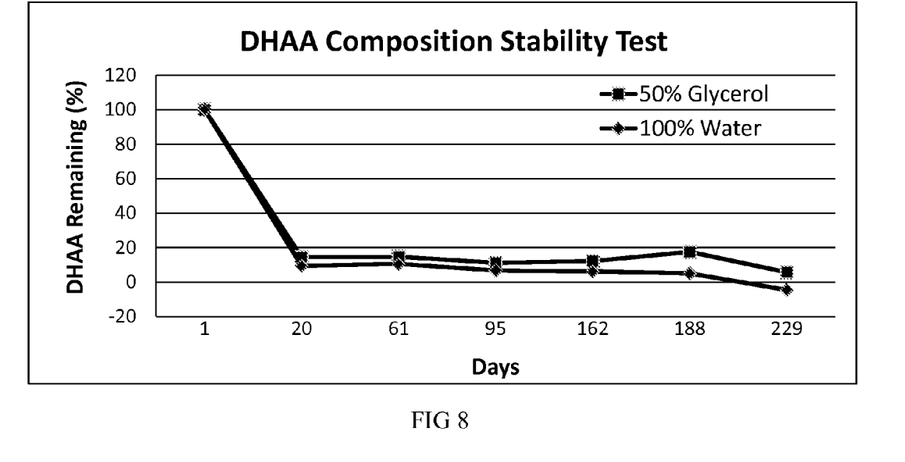
Figure 9:
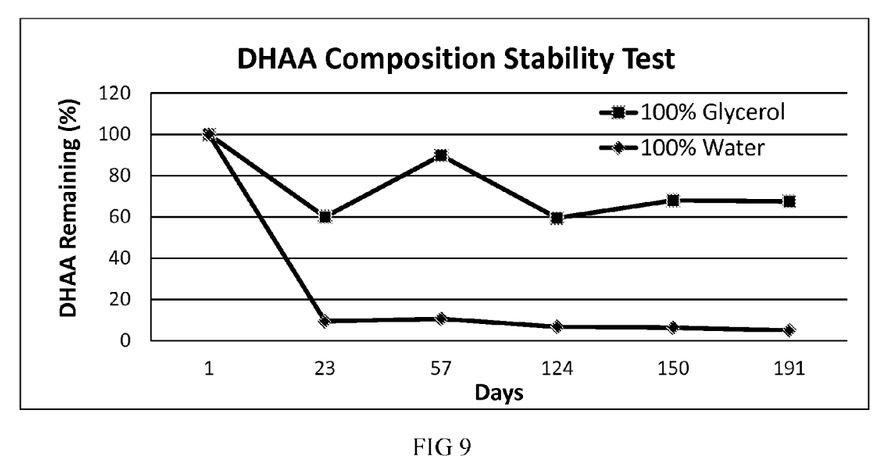
FIG. 9 shows the DHAA stability of the composition described in Example 2 as compared with DHAA prepared in water.
Figure 10:
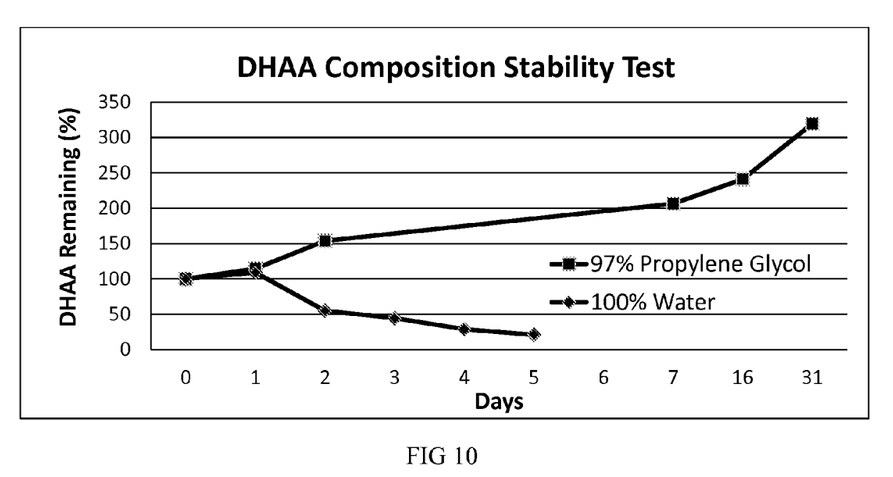
FIGS. 10 to 15 show the DHAA stability of the compositions described in Example 3 as compared with DHAA prepared similarly in water.
Figure 11:
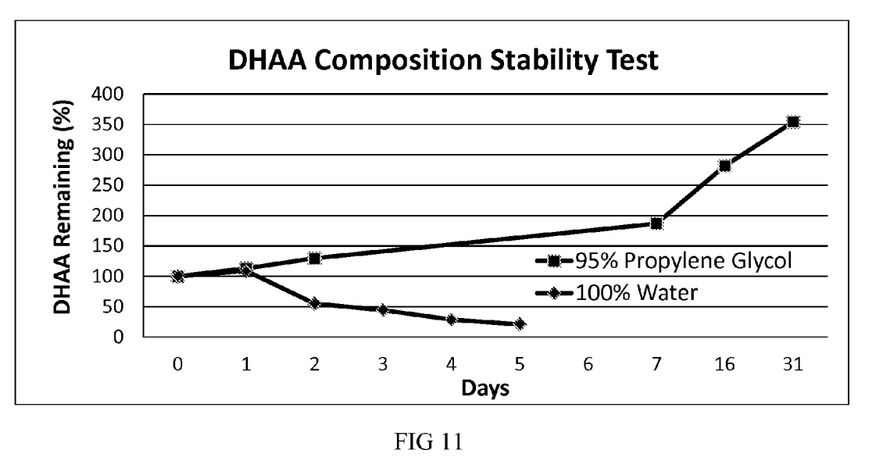
Figure 12:
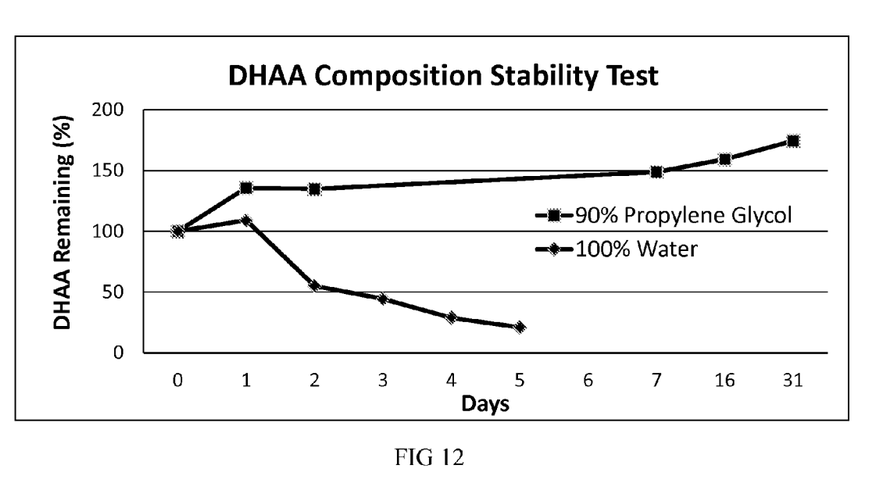
Figure 13:
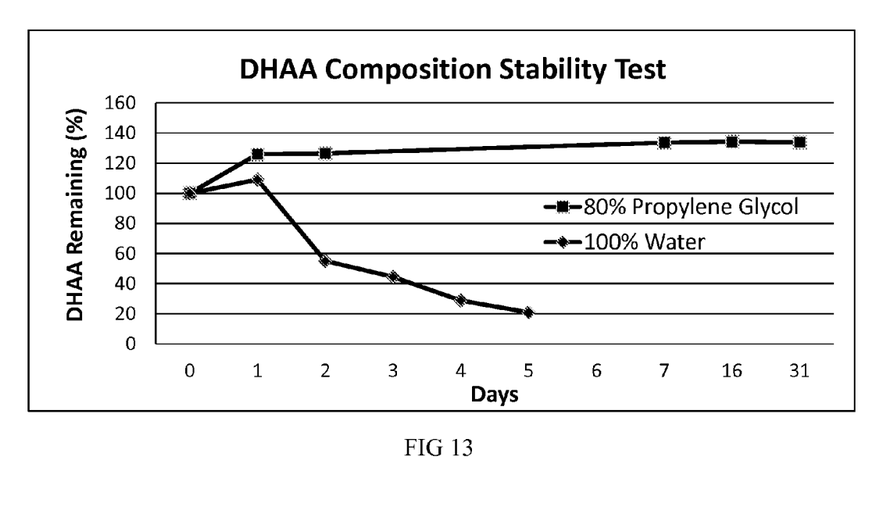
Figure 14:
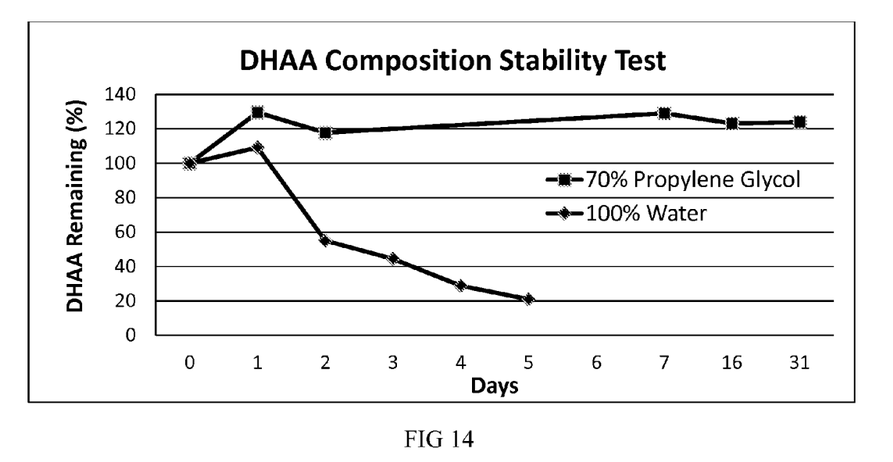
Figure 15:
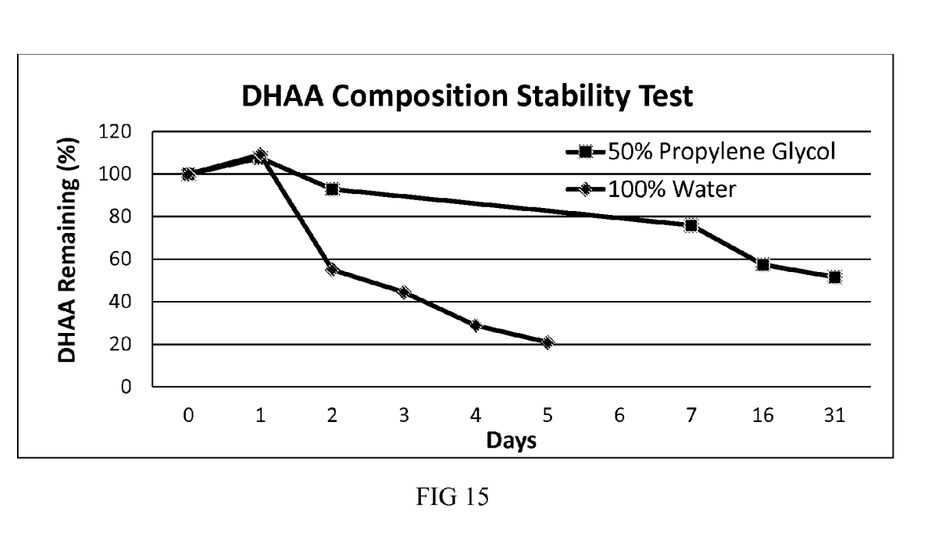

FIG. 9 shows the results of the stability testing of this solution, and for comparison also shows the stability of a DHAA solution prepared in purified water (labeled "100% Water"). It can be seen that DHAA in glycerol produced by an alternative oxidation method shows excellent long-term stability.

EXAMPLE 3

In another embodiment, stable DHAA compositions are produced by oxidizing AA dissolved in water using Fenton's Reagent as the oxidizing method, and then combining the water solution with propylene glycol such that the final concentration of polyol is 50% or greater.

AA was dissolved in purified water to give a highly concentrated solution, and then sufficient 30% hydrogen peroxide was added to oxidize about half of the AA. Iron to catalyze the reaction was provided by addition of ferrous sulfate. Oxidation of the AA was monitored by spectrometry until the expected amount of AA had been oxidized. This solution was labeled "100% Water." Portions of this solution were combined with portions of pure, USP grade propylene glycol to produce solutions of "97% Propylene Glycol," "95% Propylene Glycol," "90% Propylene Glycol," "80% Propylene Glycol," "70% Propylene Glycol," and "50% Propylene Glycol." For example, 3 parts by volume of the "100% Water" solution were combined with 97 parts by volume propylene glycol to yield the "97% Propylene Glycol" solution.

Aliquots of each of the solutions prepared above were placed in translucent, screw-capped polyethylene vials and were stored at room temperature. No attempt was made to further protect the vials from ambient indoor light, and each vial contained a headspace of normal air. Each vial was periodically opened to remove a sample for stability testing over the next 31 days. The concentration of DHAA in each sample was measured by spectrometry on each testing day. The initial DHAA concentration of each solution was recorded and assigned a value of 100% (Day 0), and the concentration on each subsequent stability test day was calculated as the percent remaining of the initial concentration.

FIGS. 10 through 15 show the results of stability testing of the various propylene glycol-containing solutions; each graph also shows the result of the "100% Water" solution for comparison. It can be seen that DHAA decomposes rapidly in water; after only 5 days, less than 20 percent of the initial amount of DHAA remains. By contrast, DHAA is preserved very well in solutions containing high concentrations of propylene glycol. In fact, the DHAA concentration in many of these solutions actually increased significantly over time, a remarkable and unexpected discovery. We believe this phenomenon can be explained this way: residual AA continues to oxidize while the DHAA is stabilized and therefore accumulates in the solution. The spectrophotometric measurements support this explanation, but we do not wish to be bound by this explanation.

Example 3 demonstrates that stable DHAA compositions may be prepared using a third alternative oxidation method as compared with the first two examples, and also demonstrates that an alternative polyol solvent can be used.

Conclusion, Ramifications, and Scope

While the above description contains many specificities, these should not be construed as limitations on the scope of the invention, but rather as exemplification of preferred embodiments. The compositions can be prepared using various methods and ingredients as mentioned, and their equivalents. Polyol solvents are known to be antimicrobial in high concentrations and therefore the compositions of the invention generally do not require preservatives. Polyol solvents are also capable of dissolving substances that are not soluble in water, so are capable of solubilizing not only AA and DHAA but additional dietary or skin-enhancing ingredients such as vitamin E. Many polyol solvents are excellent skin-enhancing substances in their own right, such as glycerol which is commonly utilized in skin care products as a humectant. Many polyol solvents are not only safe for ingestion, but in fact have a pleasant, sweet flavor. Thus the compositions have favorable properties that are synergistic with their use as dietary supplements, skin-enhancers, concentrates, or research solutions. Accordingly, the scope of the invention should be determined not by the embodiments illustrated, but by the appended claims and their equivalents.

We claim:

1. A liquid vitamin C concentrate composition, comprising:
    (a) at least dehydroascorbic acid (DHAA), and
    (b) at least one pharmacologically acceptable liquid organic polyol solvent for said DHAA; wherein said polyol solvent comprises about 50% or greater of the total weight of said composition, further comprising a ratio of ascorbic acid (AA) to DHAA of about 1:1 to greater than 99% DHAA.

2. The liquid concentrate composition of claim 1, wherein said liquid organic polyol solvent comprises glycerol and/or propylene glycol.

3. The liquid concentrate composition of claim 1 wherein said composition includes a pharmacologically acceptable vitamin E compound.

4. A vitamin C product prepared from the concentrate composition of claim 1.

5. The method for application of vitamin C comprising introducing to the human body or the body of an animal the composition of claim 1.

6. A liquid dehydroascorbic acid (DHAA) composition, comprising:
    (a) at least DHAA, and
    (b) at least one pharmacologically acceptable liquid organic polyol solvent for said DHAA; wherein said polyol solvent comprises about 50% or greater of the total weight of said composition, further comprising a ratio of ascorbic acid (AA) to DHAA of about 1:1 to greater than 99% DHAA.

7. The liquid dehydroascorbic acid composition of claim 6 comprising a ratio of AA to DHAA of about 1:1.

8. The liquid dehydroascorbic acid composition of claim 6 wherein said polyol solvent comprises about 70% or greater of the total weight of said composition.

9. The liquid dehydroascorbic acid composition of claim 6 wherein dehydroascorbic acid comprises about 0.75% to about 15% of said composition.

10. The liquid dehydroascorbic acid composition of claim 6 prepared by oxidizing ascorbic acid in solution by exposing said solution to halogen or ozone or oxygen/activated charcoal or Fenton's Reagent or ascorbic acid oxidase enzyme or a gas containing oxygen and/or ozone wherein said gas contains said oxygen and/or ozone at concentrations greater than found in typical atmospheric air.

11. The liquid dehydroascorbic acid composition of claim 6 prepared by oxidizing ascorbic acid and combining with a substantially pure polyol.

12. The liquid dehydroascorbic acid composition of claim 6 which is a dietary supplement and/or for topical application.

13. The liquid dehydroascorbic acid composition of claim 6 comprising a dietary acceptable polyol.

14. The liquid dehydroascorbic acid composition of claim 6 comprising a topically acceptable polyol.

15. The liquid dehydroascorbic acid composition of claim 6 comprising USP glycerol.

16. The liquid dehydroascorbic acid composition of claim 6 in a polyethylene container.

17. The liquid dehydroascorbic acid composition of claim 6 wherein said dehydroascorbic acid is stable at room temperature.

18. The liquid dehydroascorbic acid composition of claim 6 wherein the level of DHAA is stable or increases.

* * * * *